(12) United States Patent
Nakamura

(10) Patent No.: US 10,470,666 B2
(45) Date of Patent: Nov. 12, 2019

(54) PHOTOACOUSTIC APPARATUS, INFORMATION ACQUIRING APPARATUS, INFORMATION ACQUIRING METHOD, AND STORAGE MEDIUM

(71) Applicant: CANON KABUSHIKI KAISHA, Tokyo (JP)

(72) Inventor: Yoshiko Nakamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 240 days.

(21) Appl. No.: 15/383,785

(22) Filed: Dec. 19, 2016

(65) Prior Publication Data

US 2017/0172420 A1    Jun. 22, 2017

(30) Foreign Application Priority Data

Dec. 21, 2015   (JP) ................................. 2015-249069

(51) Int. Cl.
  *A61B 5/00*   (2006.01)
  *A61B 5/145*  (2006.01)
(52) U.S. Cl.
  CPC ........ *A61B 5/0095* (2013.01); *A61B 5/14542* (2013.01); *A61B 5/4312* (2013.01); *A61B 5/14532* (2013.01); *A61B 5/4872* (2013.01)
(58) Field of Classification Search
  None
  See application file for complete search history.

(56) References Cited

U.S. PATENT DOCUMENTS 7,864,307 B2 *  1/2011  Fukutani ............. A61B 5/0073
                                           356/73
2003/0167002 A1  9/2003  Nagar
2014/0148683 A1  5/2014  Fukutani
(Continued)

FOREIGN PATENT DOCUMENTS

CN     1650794 A     8/2005
CN   101677765 A     3/2010
CN   102256536 A    11/2011
(Continued)

OTHER PUBLICATIONS

Kazunori Suzuki, et al. "Quantitative Measurement of Optical Parameters in Normal Breasts Using Time-Resolved Spectroscopy: In Vivo Results of 30 Japanese Women", Journal of Biomedical Optics 1(3), 330-334 (Jul. 1996).
(Continued)

*Primary Examiner* — Brian T Gedeon
(74) *Attorney, Agent, or Firm* — Canon U.S.A. Inc., IP Division

(57) ABSTRACT

A photoacoustic apparatus includes a light irradiation unit configured to irradiate an object with light; a receiving unit configured to convert a photoacoustic wave generated from the object irradiated with the light from the light irradiation unit into an electric signal; an optical coefficient acquiring unit configured to acquire optical coefficient information of the object; a sound speed acquiring unit configured to acquire sound speed information of the object by using the optical coefficient information acquired by the optical coefficient acquiring unit; and an object information acquiring unit configured to acquire object information by using the electric signal and the sound speed information.

12 Claims, 10 Drawing Sheets

(56) References Cited

U.S. PATENT DOCUMENTS

2014/0198606 A1 7/2014 Morscher

FOREIGN PATENT DOCUMENTS

| CN | 102640014 A | 8/2012 |
| CN | 102740776 A | 10/2012 |
| CN | 102961138 A | 3/2013 |
| JP | 2009-018153 A | 1/2009 |
| JP | 2010-088627 A | 4/2010 |
| JP | 2010-512940 A | 4/2010 |
| JP | 2011-206192 A | 10/2011 |

OTHER PUBLICATIONS

Minghua Xu, "Universal back-projection algorithm for photoacoustic computed tomography", Physical Review E 71, 016706(1-7) (2005).

* cited by examiner

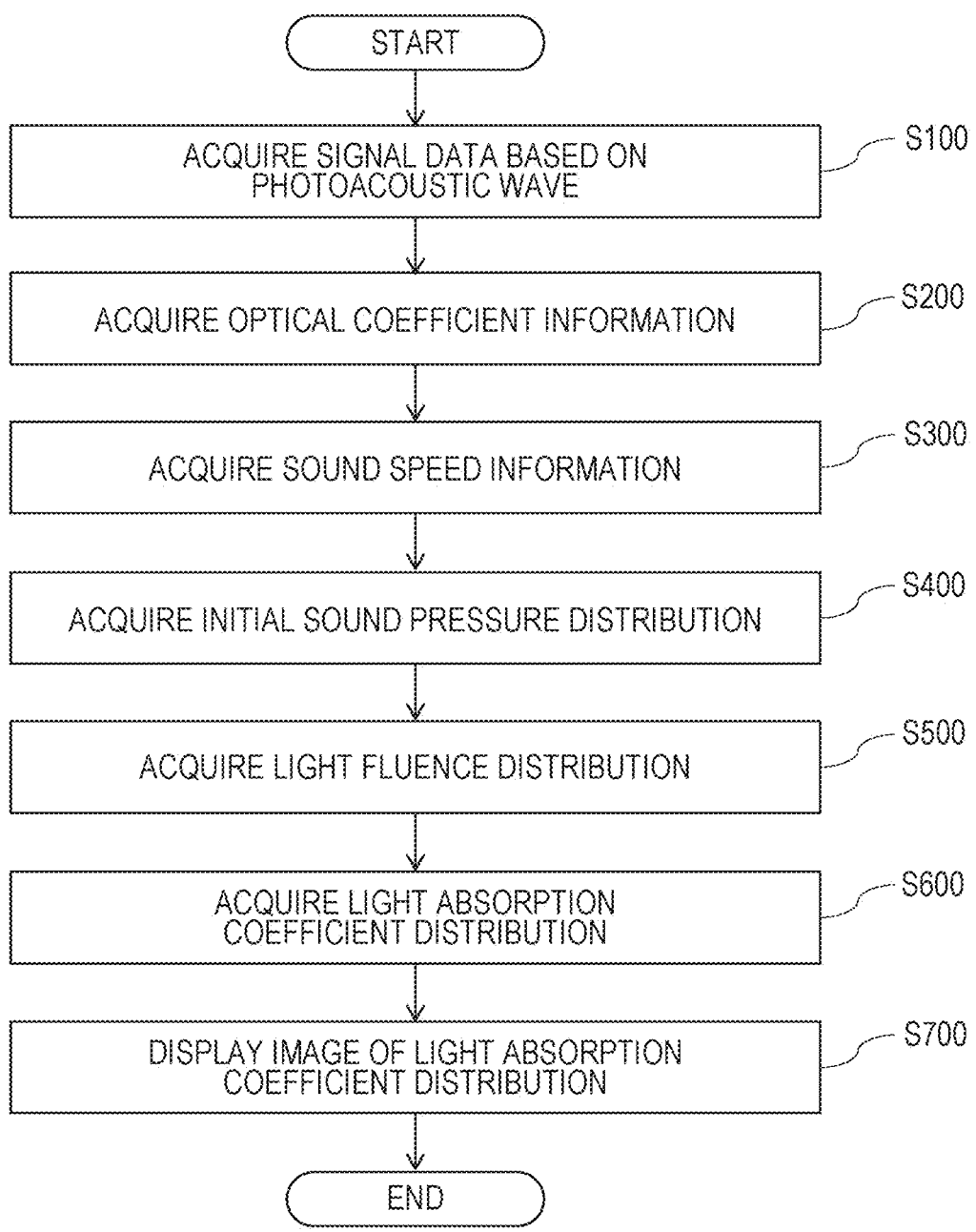

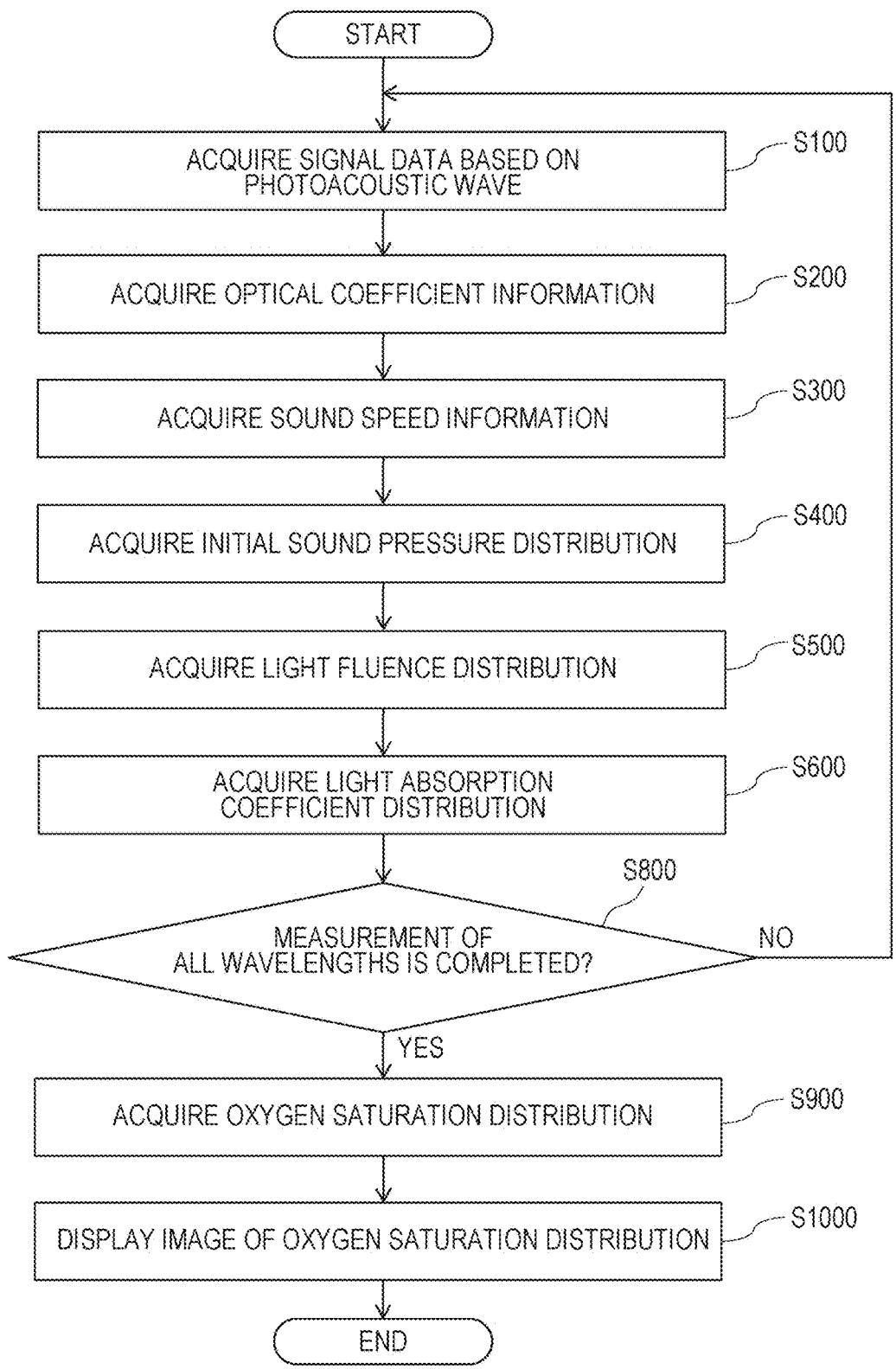

PHOTOACOUSTIC APPARATUS, INFORMATION ACQUIRING APPARATUS, INFORMATION ACQUIRING METHOD, AND STORAGE MEDIUM

BACKGROUND OF THE INVENTION

Field of the Invention

The present invention relates to a photoacoustic apparatus, an information acquiring apparatus, an information acquiring method, and a storage medium.

Description of the Related Art

There has been suggested a clinical application of an apparatus that estimates sound speed information of an object such as a living body. As a method of estimating sound speed information of an object, PCT Japanese Translation Patent Publication No. 2010-512940 suggests a method of estimating the sound speed in a living body from a measurement result of ultrasound passing through the living body.

SUMMARY OF THE INVENTION

The present invention provides a new method of acquiring sound speed information.

The present invention provides a photoacoustic apparatus including a light irradiation unit configured to irradiate an object with light; a receiving unit configured to convert a photoacoustic wave generated from the object irradiated with the light from the light irradiation unit into an electric signal; an optical coefficient acquiring unit configured to acquire optical coefficient information of the object; a sound speed acquiring unit configured to acquire sound speed information of the object by using the optical coefficient information acquired by the optical coefficient acquiring unit; and an object information acquiring unit configured to acquire object information by using the electric signal and the sound speed information.

Further features of the present invention will become apparent from the following description of exemplary embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIG. 3 is a flowchart of an operation of the photoacoustic apparatus according to the first embodiment.

FIG. 10 is a flowchart of an operation of a photoacoustic apparatus according to a third embodiment.

DESCRIPTION OF THE EMBODIMENTS

Desirable embodiments of the invention are described below with reference to the drawings. The dimensions, materials, and shapes of components described below, relative arrangement of the components, and so forth can be changed in accordance with the configuration of an apparatus to which the invention is applied and various conditions. Hence, the scope of the invention should not be limited to the description given below.

First Embodiment

In this embodiment, an example is described, in which sound speed information acquired by a new method is used for photoacoustic imaging (PAI).

A photoacoustic apparatus irradiates an object with pulsed light, receives a photoacoustic wave (an ultrasound) generated as the result of a tissue in the object absorbing the energy of the irradiation light, and generates a generation sound pressure (initial sound pressure) distribution of the photoacoustic wave. At this time, since the photoacoustic apparatus generates the initial sound pressure distribution on the basis of the reception signal of the photoacoustic wave, the photoacoustic apparatus requires the sound speed in the propagation path of the acoustic wave. That is, the photoacoustic apparatus requires the sound speed (the sound speed information of the object) when the photoacoustic wave propagates in the object.

Owing to this, in this embodiment, a new method of acquiring sound speed information of an object, used for photoacoustic imaging, is described. In this embodiment, sound speed information of an object is acquired on the basis of the relationship between optical coefficient information and sound speed information, found by the inventor.

Information acquired by use in photoacoustic imaging according to this embodiment is, for example, a light absorption coefficient or information relating to the concentration of a substance configuring an object. The information relating to the concentration of a substance is, for example, the concentration of oxyhemoglobin, the concentration of deoxyhemoglobin, the concentration of total hemoglobin, or oxygen saturation. The concentration of total hemoglobin is the sum of the concentrations of oxyhemoglobin and deoxyhemoglobin. The oxygen saturation is the ratio of oxyhemoglobin to all hemoglobin. In this embodiment, distribution information representing the value of the above-described information at each position (each position in a two-dimensional or three-dimensional space) of the object, and a representative value (an average or another value) of the above-described information of the object are acquired as object information.

Figure 1:
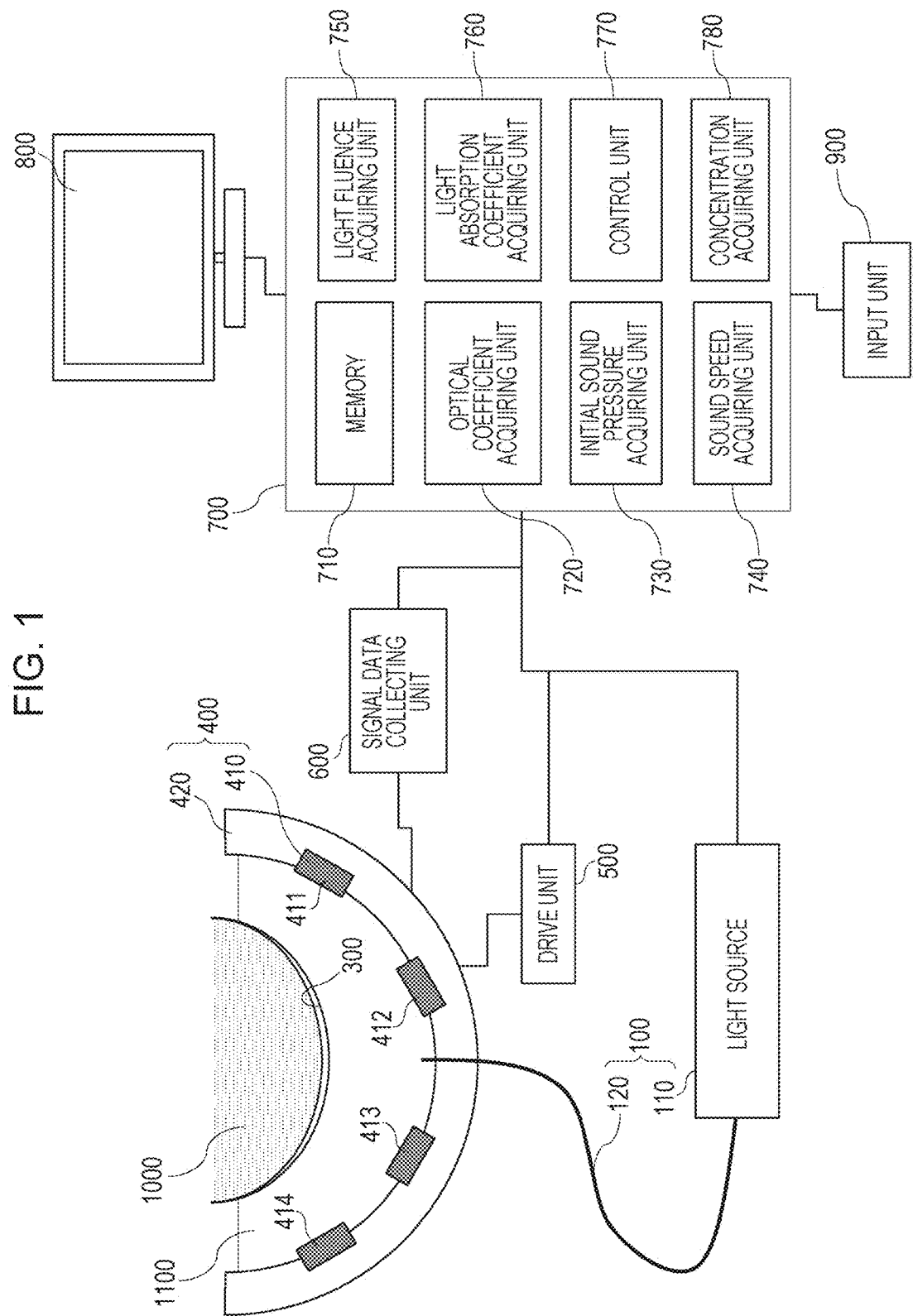
FIG. 1 is a schematic illustration showing a configuration of a photoacoustic apparatus according to a first embodiment.

FIG. 1 is a schematic illustration showing a photoacoustic apparatus according to this embodiment. The photoacoustic apparatus includes a light irradiation unit 100, a holding unit 300, a receiving unit 400, a drive unit 500, a signal data collecting unit 600, a computer 700, a display unit 800, and an input unit 900. An object to be measured is an object 1000.

Light Irradiation Unit 100

The light irradiation unit 100 includes a light source 110 that emits light, and an optical system 120 that guides the light emitted from the light source 110 to the object 1000.

The light source 110 may be desirably a pulsed light source that can generate pulsed light in nanosecond to microsecond order. The pulse width of the light may be about 1 to about 100 nanoseconds. Also, the wavelength of the light may be in a range from about 400 nm to about 1600 nm. If a blood vessel near a surface of a living body is imaged with high resolution, a wavelength largely absorbed by the blood vessel (in a range from 400 nm to 700 nm) may be used. In contrast, if a deep portion of the living body is imaged, a wavelength (in a range from 700 nm to 1100 nm) typically less absorbed by a background tissue (for example, water and fat) of the living body may be used.

For the light source 110, a laser or a light-emitting diode may be used. Also, when measurement is performed by using light with a plurality of wavelengths, a wavelength-changeable light source may be used. If an object is irradiated with a plurality of wavelengths, a plurality of light sources that generate light with mutually different wavelengths may be prepared, and an object may be alternately irradiated with the light from the respective light sources. Even if the plurality of light sources are used, the light sources are collectively expressed as a light source. For the laser, any one of various lasers including a solid-state laser, a gas laser, a dye laser, and a semiconductor laser may be used. A pulse laser, such as a Nd:YAG laser or an alexandrite laser, may be desirably used. Alternatively, a Ti:sa laser or an optical parametric oscillators (OPO) laser using Nd:YAG laser light as exciting light may be used.

The optical system 120 can use optical elements such as a lens, a mirror, an optical fiber, and so forth. When a breast or the like serves as the object 1000, the beam diameter of pulsed light is desirably spread and irradiated, and hence the light emitting portion of the optical system 120 may be configured of a diffusing plate or the like that diffuses light. In contrast, in a photoacoustic microscope, to increase the resolution, the light emitting portion of the optical system 120 may be configured of a lens or the like, and a beam may be focused and irradiated.

Alternatively, the light irradiation unit 100 may not include the optical system 120, and the light source 110 may directly irradiate the object 1000 with the light.

Holding Unit 300

The holding unit 300 is used for holding the shape of the object during measurement. Since the holding unit 300 holds the object 1000, the movement of the object can be restricted, and the position of the object 1000 can be held within the holding unit 300. For the material of the holding unit 300, PET or the like can be used.

The holding unit 300 may be desirably formed of a material having a certain hardness that can hold the object 1000. The holding unit 300 may be formed of a material that transmits light used for measurement. The holding unit 300 may be formed of a material having an impedance substantially equivalent to that of the object 1000. If an object having a curved surface such as a breast serves as the object 1000, the holding unit 300 may be molded in a recessed shape. In this case, the object 1000 can be inserted into the recessed portion of the holding unit 300.

However, the photoacoustic apparatus according to this embodiment may not include the holding unit 300. Also, the photoacoustic apparatus according to this embodiment may not include the holding unit 300 and may have an opening that allows a breast to be inserted.

Receiving Unit 400

The receiving unit 400 includes a receiving element group 410 and a support body 420 that supports the receiving element group 410. The receiving element group 410 includes receiving elements 411 to 414 that receive acoustic waves and outputs electric signals.

A member that configures each of the receiving elements 411 to 414 can use a piezoelectric ceramic material represented by lead zirconate titanate (PZT), or a polymer piezoelectric film material represented by polyvinylidene fluoride (PVDF). Alternatively, an element other than a piezoelectric element may be used. For example, a capacitive transducer (capacitive micro-machined ultrasonic transducers (CMUT)), or a transducer using a Fabry-Perot interferometer may be used. It is to be noted that any transducer may be employed as a receiving element as long as the receiving element can receive an acoustic wave and output an electric signal.

The support body 420 may be formed of a metal material or other material having high mechanical strength. In this embodiment, the support body 420 has a hemispherical shell shape, and is configured to support the receiving element group 410 on the hemispherical shell. In this case, the directional axes of the respective receiving elements are collected at a position near the center of the curvature of the hemisphere. When imaging is performed by using an electric signal group output from these receiving elements, the image quality at the position near the center of the curvature is high. However, the support body 420 may have any configuration as long as the support body 420 can support the receiving element group 410.

Signal Data Collecting Unit 600

The signal data collecting unit 600 includes an amplifier that amplifies an electric signal being an analog signal output from each of the receiving elements 411 to 414, and an A/D converter that converts the analog signal output from the amplifier into a digital signal. The digital signal output from the signal data collecting unit 600 is stored in a memory 710 in the computer 700. The signal data collecting unit 600 is also called data acquisition system (DAS). In this specification, an electric signal is a concept including an analog signal and a digital signal.

Computer 700

The computer 700 includes the memory 710, an optical coefficient acquiring unit 720, an initial sound pressure acquiring unit 730, a sound speed acquiring unit 740, a light fluence acquiring unit 750, a light absorption coefficient acquiring unit 760, a control unit 770, and a concentration acquiring unit 780.

The memory 710 can be configured of a non-temporary storage medium, such as a magnetic disk or a flash memory. Alternatively, the memory 710 may be a volatile medium such as a dynamic random access memory (DRAM). It is to be noted that a storage medium storing a program is a non-temporary storage medium.

Units having arithmetic functions, such as the optical coefficient acquiring unit 720, the sound speed acquiring unit 740, the initial sound pressure acquiring unit 730, the light fluence acquiring unit 750, the light absorption coefficient acquiring unit 760, and the concentration acquiring unit 780 each can be configured of a processor being a CPU or a graphics processing unit (GPU); or an arithmetic circuit such as a field programmable gate array (FPGA) chip. These units each may not be configured of a single processor or a single arithmetic circuit, and may be configured of a plurality of processors or a plurality of arithmetic circuits.

The control unit 770 is configured of an arithmetic element such as a CPU. The control unit 770 receives signals by various operations, such as start of imaging from the input unit 900, and controls respective configurations of the photoacoustic apparatus. Also, the control unit 770 reads out a program code stored in the memory 710, and controls operations of respective configurations of the photoacoustic apparatus.

The computer 700 is a device that stores a digital signal output from the signal data collecting unit 600 and acquires object information on the basis of the stored digital signal. Processing executed by the computer 700 will be described later in detail.

It is to be noted that respective functions of the computer 700 may be configured of different pieces of hardware. Alternatively, the receiving unit 400, the signal data collecting unit 600, and the computer 700 may be configured of a single piece of hardware. Still alternatively, at least portions of the respective configurations may be configured of a single piece of hardware. For example, the receiving unit 400 and the signal data collecting unit 600 may be configured of a single piece of hardware.

Figure 2:
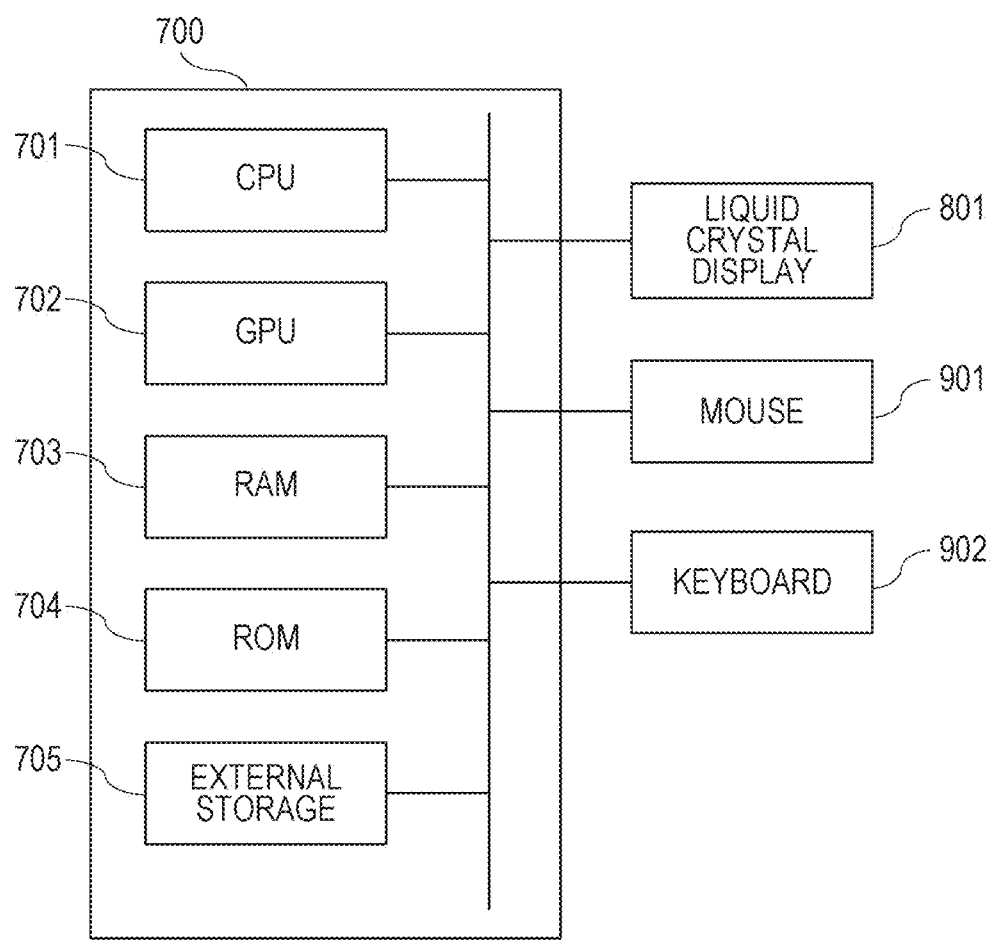
FIG. 2 is an illustration showing a specific example of a computer according to the first embodiment.

FIG. 2 shows a specific configuration of the computer 700 according to this embodiment. The computer 700 according to this embodiment includes a CPU 701, a GPU 702, a RAM 703, a ROM 704, and an external storage 705. Also, a liquid crystal display 801 serving as the display unit 800, and a mouse 901 and a keyboard 902 serving as the input unit 900 are connected with the computer 700.

Display Unit 800

The display unit 800 is a display, such as a liquid crystal display or an organic electro luminescence (EL) display. The display unit 800 is a device that displays an image based on, for example, sound speed information, optical coefficient information, or object information acquired by the computer 700, a numerical value of a specific position, and so forth. The display unit 800 may display GUI for operating the image and device.

Input Unit 900

The input unit 900 can be configured of, for example, a mouse and a keyboard operable by a user. Alternatively, the display unit 800 may be configured of a touch panel, and the display unit 800 may serve as the input unit 900.

The respective configurations of the photoacoustic apparatus may be configured of respectively different apparatuses, or may be configured of a single integrated apparatus. Alternatively, at least a partial configuration of the photoacoustic apparatus may be configured as a single integrated apparatus.

Acoustic Matching Material 1100

An acoustic matching material 1100 is described although it is not a configuration of the photoacoustic apparatus. For the acoustic matching material 1100, water, ultrasonic gel, or the like, is used. The acoustic matching material 1100 is for allowing an acoustic wave to propagate between the holding unit 300 and the receiving elements 411 to 414. The acoustic matching material 1100 may be a material that little attenuates the acoustic wave. If irradiation light is transmitted through the acoustic matching material, the acoustic matching material may be transparent to the irradiation light.

An operation of a photoacoustic apparatus according to this embodiment is described below with reference to a flowchart in FIG. 3.

S100: Step of Acquiring Signal Data Based on Photoacoustic Wave

The light emitted from the light source 110 is guided by a bundle fiber serving as the optical system 120 to the object 1000. The optical system 120 irradiates the object 1000 with the light through the holding unit 300. An optical absorber in the object 1000 absorbs the irradiation light, expands in volume, and generates a photoacoustic wave. This photoacoustic wave propagates through the object 1000 and the acoustic matching material 1100, and reaches the receiving element group 410. The respective receiving elements 411 to 414 receive this photoacoustic wave and output electric signals. Thus, the receiving element group 410 outputs an electric signal group. An electric signal output from a receiving element is a signal in time series representative of a variation with time of the pressure of the photoacoustic wave which has reached the receiving element.

The signal data collecting unit 600 converts the electric signal group being an analog signal group output from the receiving element group 410 into a digital signal group. This digital signal group is stored in the memory 710. That is, signal data based on the photoacoustic wave is stored in the memory 710.

Also, the drive unit 500 may move the receiving unit 400, and the receiving unit 400 may receive the photoacoustic wave at a plurality of different positions. The drive unit 500 includes a motor such as a stepping motor that generates a drive force, a drive mechanism that transmits the drive force, and a position sensor that detects position information of the receiving unit 400. For the drive mechanism, for example, a lead screw mechanism, a link mechanism, a gear mechanism, or a hydraulic mechanism may be used. For the position sensor, for example, an encoder or a potentiometer such as a variable resistor may be used. The drive unit 500 can change the relative positions between the object 1000 and the receiving unit 400 first-dimensionally, second-dimensionally, or third-dimensionally.

The drive unit 500 may fix the receiving unit 400 and move the object 1000 as long as the drive unit 500 can change the relative positions between the object 1000 and the receiving unit 400. To move the object 1000, a configuration is conceivable in which the object 1000 is moved by moving the holding unit 300 holding the object 1000. Alternatively, the drive unit 500 may move both the object 1000 and the receiving unit 400. Also, the drive unit 500 may move the relative positions continuously or by step and repeat.

S200: Step of Acquiring Optical Coefficient Information

The optical coefficient acquiring unit 720 acquires optical coefficient information of the object. The optical coefficient acquiring unit 720 may acquire the optical coefficient information of the object by any of known methods.

The optical coefficient information according to this embodiment indicates at least one representative value of a light absorption coefficient $\mu_a$, a reduced scattering coefficient $\mu_s'$, and an effective attenuation coefficient $\mu_{\mathit{eff}}$ acquired on the basis of the assumption that the object 1000 is a uniform medium. That is, the optical coefficient information of the object in this embodiment indicates a representative value of an optical coefficient acquired when the optical coefficient at any position of the object 1000 is assumed to be constant.

Alternatively, the optical coefficient acquiring unit 720 may acquire the optical coefficient information of the object by analyzing object information (photoacoustic image data) as distribution information generated from the signal data based on the photoacoustic wave stored in the memory 710. For example, the optical coefficient acquiring unit 720 may acquire the optical coefficient information of the object on the basis of signal data resulting from a photoacoustic wave as described in Japanese Patent Laid-Open No. 2009-018153 or 2010-088627.

Yet alternatively, the optical coefficient acquiring unit 720 may acquire the optical coefficient information by receiving information input by the user using the input unit 900.

Yet alternatively, the optical coefficient acquiring unit 720 may acquire the optical coefficient information by inputting optical coefficient information of the object measured by a time-resolved spectroscopy (TRS) apparatus or a diffuse optical tomography (DOT) apparatus.

In a breast as the object 1000, the ratio of the mammary gland layer decreases with age and the fat layer becomes dominant as a rough tendency. Also, Kazunori Suzuki, JOURNAL OF BIOMEDICAL OPTICS 1(3), 330-334 (July 1996) describes that the optical coefficient changes with age. Owing to this, for example, the memory 710 may store a relational expression or a relational table between the age and optical coefficient information. In this case, when the user inputs information relating to the age by using the input unit 900, the optical coefficient acquiring unit 720 may read out the optical coefficient information corresponding to the age information from the memory 710, or may calculate the optical coefficient information in accordance with the relational expression.

With any of the above-described methods, the optical coefficient information of the object can be acquired every measurement. If the optical coefficient information of the same object has been acquired before, the previously acquired optical coefficient information may be read out from the memory 710 and acquired.

Also, optical coefficient information of a configuration other than the object (the holding unit 300 or the acoustic matching material 1100) included in the propagation path of the irradiation light may be acquired by any of the above-described known methods similarly to the optical coefficient information of the object. If the optical coefficient information of the configuration other than the object is already known, the optical coefficient information may be previously stored in the memory 710, and may be read out from the memory 710 and acquired.

In this embodiment, the representative value of the optical coefficient of the object serves as the optical coefficient information; however, distribution information representing a value of an optical coefficient at each position of the object may serve as the optical coefficient information of the object as described later in a second embodiment. Alternatively, a representative value of an optical coefficient acquired on the basis of an assumption that the propagation path of the irradiation light is entirely a uniform medium may serve as the optical coefficient information.

S300: Step of Acquiring Sound Speed Information

The memory 710 stores a relational expression or a relational table representing the relationship between the sound speed information and the optical coefficient information. The sound speed acquiring unit 740 calculates the sound speed information of the object on the basis of the optical coefficient information of the object acquired by the optical coefficient acquiring unit 720 in accordance with the relational expression stored in the memory 710. Alternatively, the sound speed acquiring unit 740 reads out the sound speed information of the object corresponding to the optical coefficient information of the object acquired by the optical coefficient acquiring unit 720, from the relational table stored in the memory 710.

The sound speed information of the object in this embodiment indicates a representative value of a sound speed in an object acquired on the basis of an assumption that the object is a uniform medium. That is, the sound speed information of the object in this embodiment indicates a representative value of a sound speed acquired when the sound speed at any position of the object 1000 is assumed to be constant.

In this embodiment, the representative value of the sound speed of the object serves as the sound speed information; however, distribution information representing a value of a sound speed at each position of the object may serve as the sound speed information of the object as described later in the second embodiment. Alternatively, a representative value of a sound speed acquired on the basis of an assumption that the propagation path of the acoustic wave is entirely a uniform medium may serve as the sound speed information.

The sound speed of a configuration other than the object may be acquired on the basis of the optical coefficient information similarly to the sound information of the object. Also, if the sound speed information of the configuration other than the object is already known, the sound speed information may be previously stored in the memory 710, and may be read out from the memory 710 and acquired.

The relationship between the sound speed information and the optical coefficient information is described now. A case where a breast is assumed as the object 1000 is described. As the result of measurement on the sound speed and optical coefficient of an object, it was found that the two parameters have correlation. The main structure of a breast includes fat and mammary glands. It is known that the breast has two layers including a fat layer and a mammary gland layer, and the ratio and distribution of these layers are different depending on the individual. Typically, the sound speed of the fat layer is in the range from 1422 to 1470 m/s, and the sound speed of the mammary gland layer is in the range from 1510 to 1530 m/s. That is, the sound speed decreases if the fat layer increases, and the sound speed increases if the mammary gland layer increases.

The optical coefficient information is affected by the blood present in the fat and the mammary glands. For example, the light absorption coefficient of hemoglobin in blood is largely affected particularly with a wavelength of around 800 nm as compared with the light absorption coefficients of the fat and the mammary glands. Owing to this, even if the blood vessel density per unit volume in a tissue is about 0.1%, a significant difference appears with respect to the light absorption coefficients of the fat and the mammary glands. Also, comparing the fat layer and mammary gland layer with each other, typically, the blood vessel density is higher in the mammary gland layer anatomically. Thus, it is conceivable that, in an object having the mammary gland layer by a large amount, the sound speed tends to be high, and the light absorption coefficient of the object with a near infrared wavelength (around 800 nm) tends to be large. As described above, it is conceivable that the relationship between the sound speed information and the optical coefficient information correlates with the tissue component in the breast.

Figure 4A:
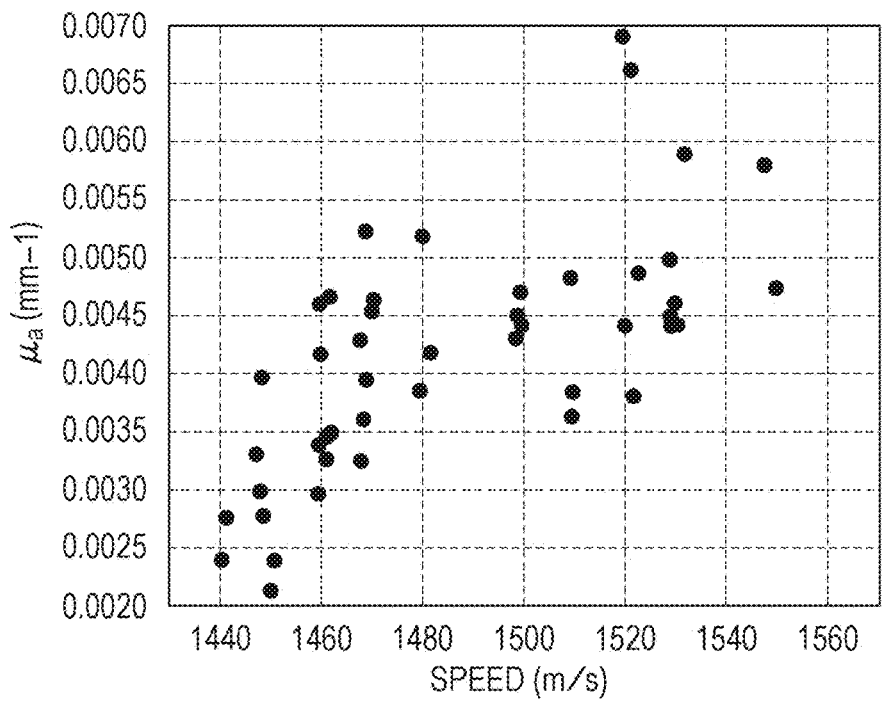
FIGS. 4A and 4B are illustrations each showing an example of a calculation result of the sound speed and the optical coefficient.
Figure 4B:
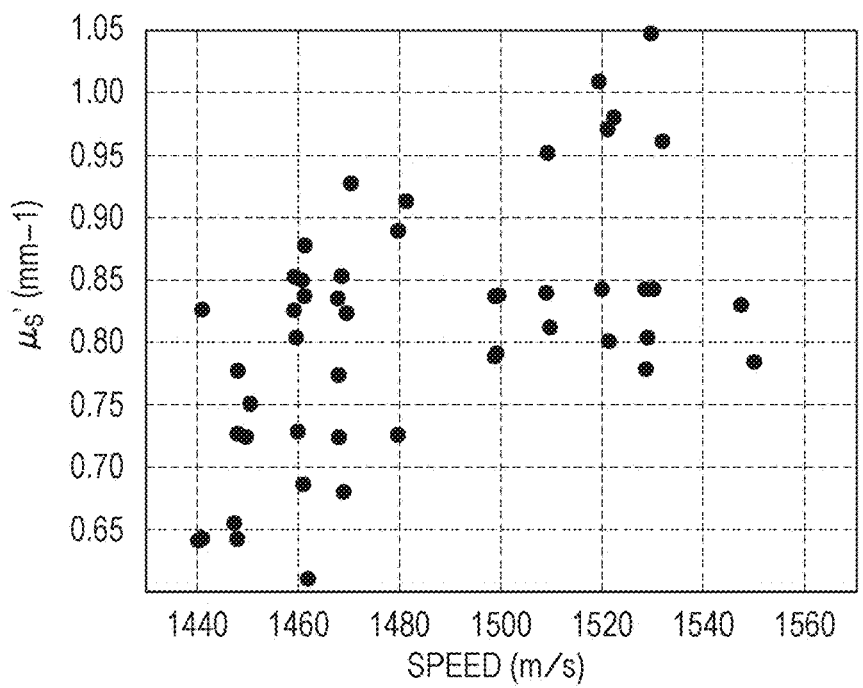

FIGS. 4A and 4B are scatter diagrams each representing the relationship between the sound speed information and the optical coefficient information ($\mu_a$ and $\mu_s'$) acquired when the structure of a breast is changed by a simulation. In FIG. 4A, the horizontal axis plots the sound speed, and the vertical axis plots the light absorption coefficient $\mu_a$. In FIG. 4B, the horizontal axis plots the sound speed, and the vertical axis plots the reduced scattering coefficient $\mu_s'$ in the breast. In this calculation, the representative values of the light absorption coefficient and the reduced scattering coefficient were calculated on the basis of an assumption that the tissue component of the object was uniform at any position. Also, the calculation was performed while randomly changing the ratio of the mammary gland layer and the fat layer, the temperature of the object, the ratio of water in the mammary gland layer, the blood vessel densities in the mammary gland layer and the fat layer, and the oxygen saturation of blood. In this calculation, the ratio of the fat was changed in a range from 30% to 90%, and the ratio of the mammary glands was changed in a range from 10% to 70%. The blood vessel density was changed in a range from 0.1% to 1.1%. The oxygen saturation was changed in a range from 70% to 100%. Also, the amount of red blood cells (hematocrit) in blood was changed in a range of 46%±6%, and the hemoglobin molar concentration was changed in a range of 0.0023876±0.00029 (M/L). The sound speed was calculated by using the statistical value of the sound speed of each structure. The light absorption coefficient $\mu_a$ and the reduced scattering coefficient $\mu_s'$ were calculated by using molar light absorption coefficients and molar reduced scattering coefficients of the fat, mammary glands, water, oxyhemoglobin, and deoxyhemoglobin with respect to the wavelength of 795 nm.

The calculation results as shown in FIGS. 4A and 4B can be stored in the memory 710, as a relational table representing the relationship between the optical coefficient information and the sound speed information. Also, an approximate expression can be obtained from the calculation results as shown in FIGS. 4A and 4B, and can be stored in the memory 710, as a relational expression representing the relationship between the optical coefficient information and the sound speed information. For example, the relational expression can be obtained by any kind of approximation, such as linear or higher-order function approximation, logarithmic function approximation, or exponential function approximation.

Figure 5A:
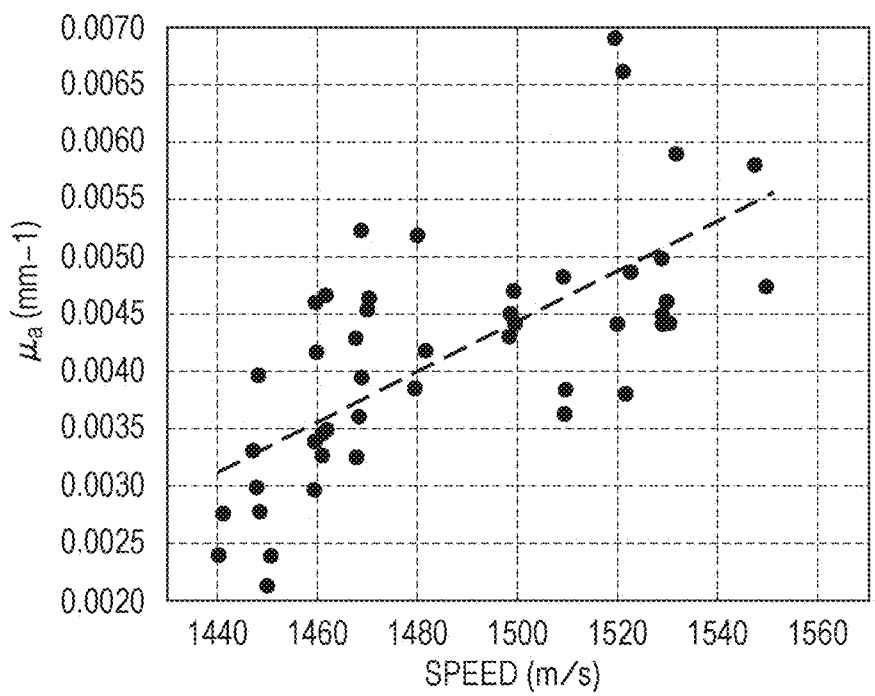
FIGS. 5A and 5B are illustrations each showing a graph of a relational expression (linear function approximate expression) between the sound speed and the optical coefficient.
Figure 5B:
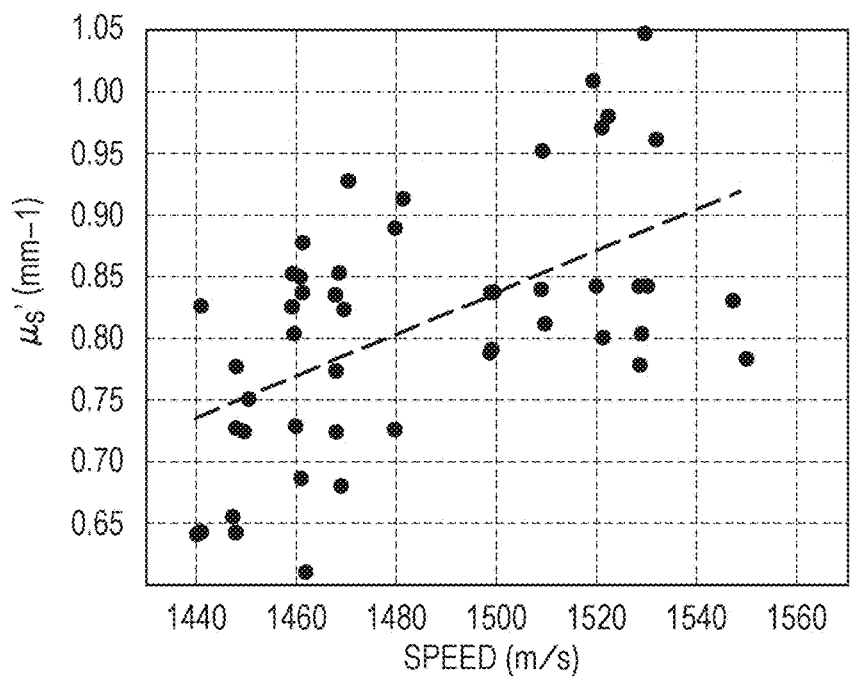

For example, by obtaining a linear function approximate expression by the least square method for the calculation results shown in FIGS. 4A and 4B, approximate expressions (graphs) shown in FIGS. 5A and 5B were acquired. Correlations R between the approximate expressions and calculation results shown in FIGS. 4A and 5B were R=0.6913 for the light absorption coefficient and R=0.5508 for the reduced scattering coefficient. In any case, a significant probability p is 0.000 or lower.

Figure 6A:
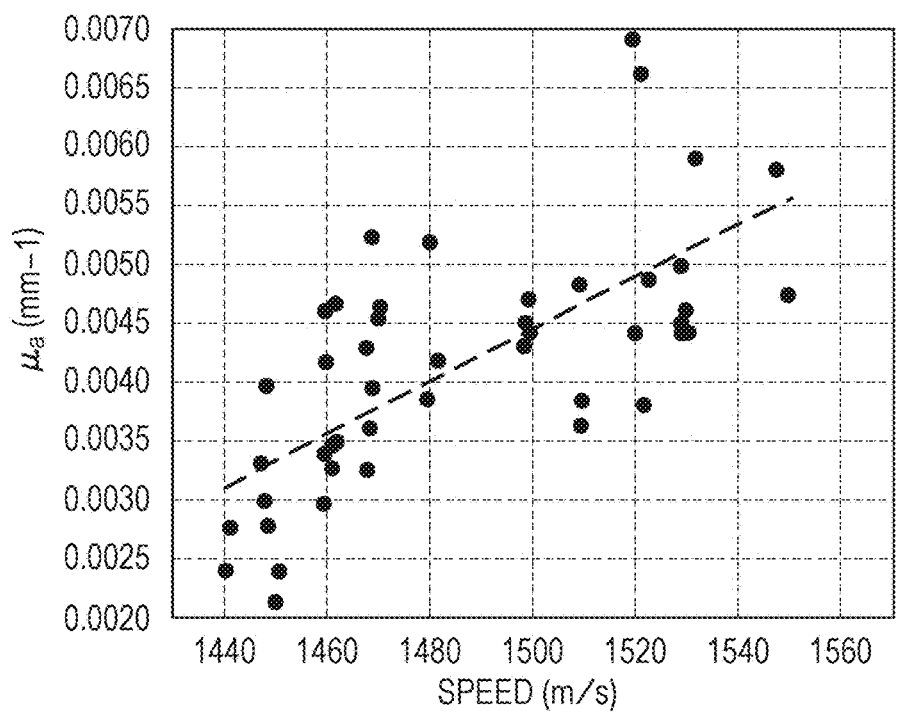
FIGS. 6A and 6B are illustrations each showing a graph of a relational expression (cubic function approximate expression) between the sound speed and the optical coefficient.
Figure 6B:
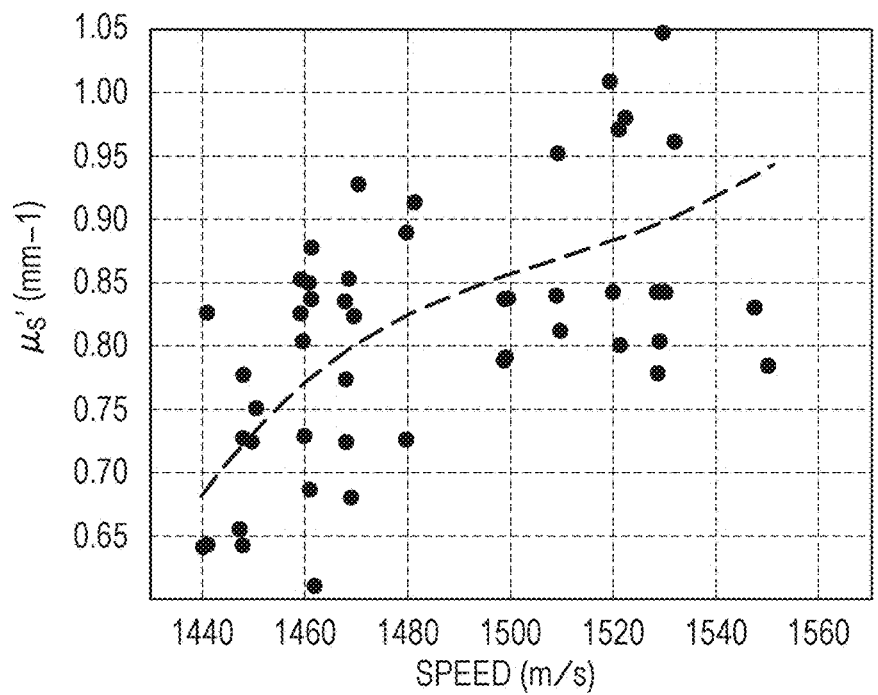

Also, by obtaining a cubic function approximate expression by the least square method for the calculation results shown in FIGS. 4A and 4B, approximate expressions (graphs) shown in FIGS. 6A and 6B were acquired. Correlations R between the approximate expressions and calculation results shown in FIGS. 6A and 6B were R=0.6928 for the light absorption coefficient and R=0.5781 for the reduced scattering coefficient. In any case, a significant probability p is 0.000 or lower.

Figure 7A:
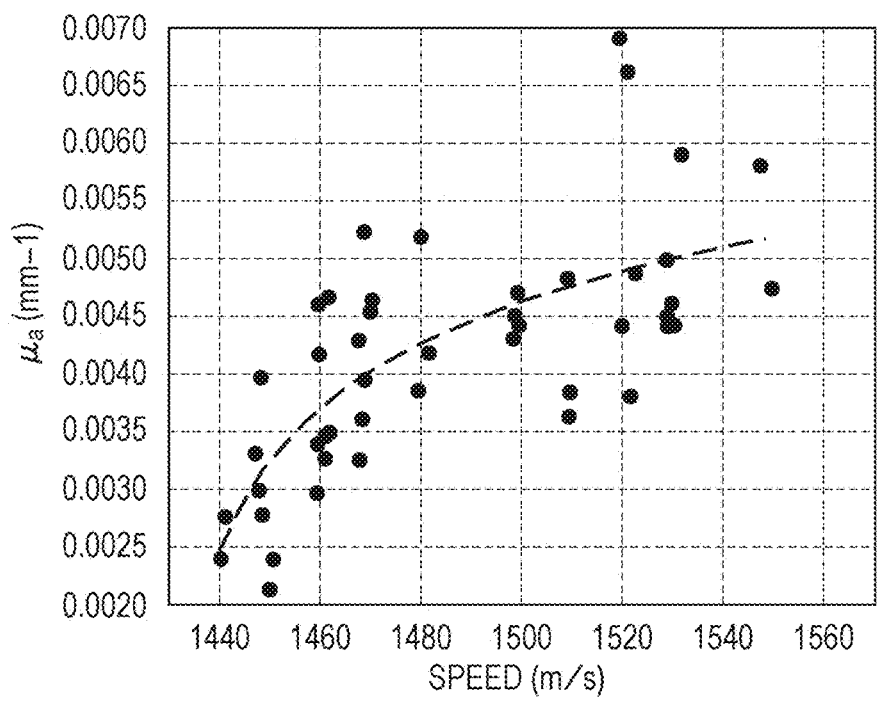
FIGS. 7A and 7B are illustrations each showing a graph of a relational expression (logarithmic function approximate expression) between the sound speed and the optical coefficient.
Figure 7B:
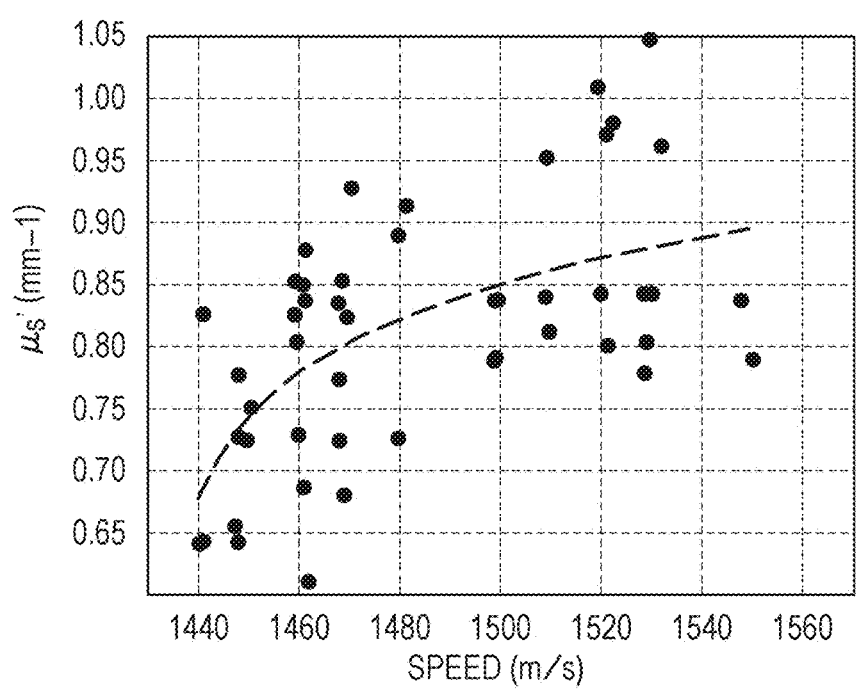

Also, by obtaining a logarithmic function approximate expression by the least square method for the calculation results shown in FIGS. 4A and 4B, approximate expressions (graphs) shown in FIGS. 7A and 7B were acquired. Correlations R between the approximate expressions and calculation results shown in FIGS. 7A and 7B were R=0.7313 for the light absorption coefficient and R=0.5948 for the reduced scattering coefficient. In any case, a significant probability p is 0.000 or lower.

Figure 8A:
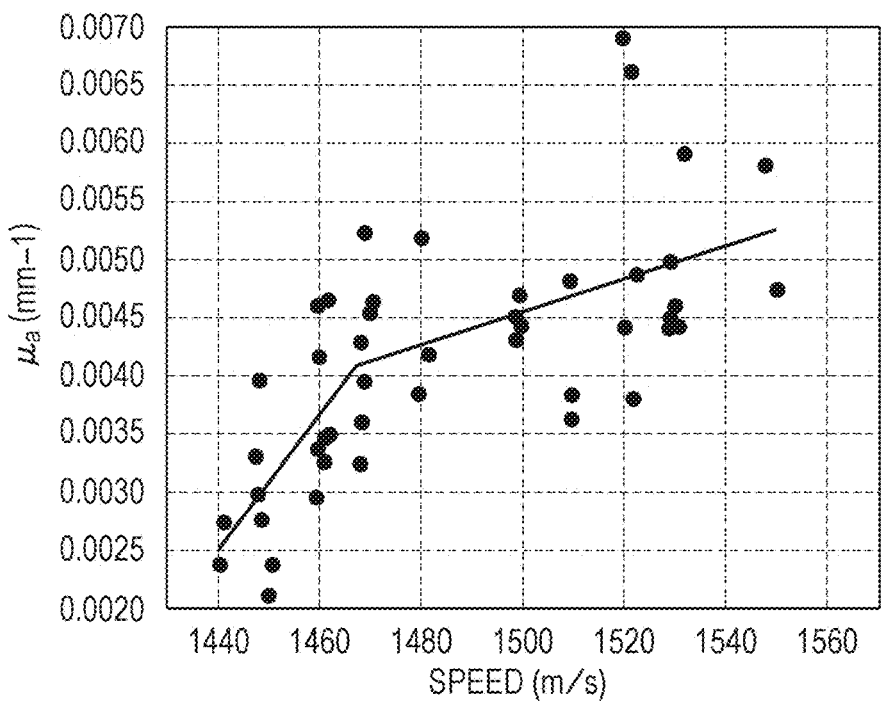
FIGS. 8A and 8B are illustrations each showing a graph of relational expressions (two linear function approximate expressions) between the sound speed and the optical coefficient.
Figure 8B:
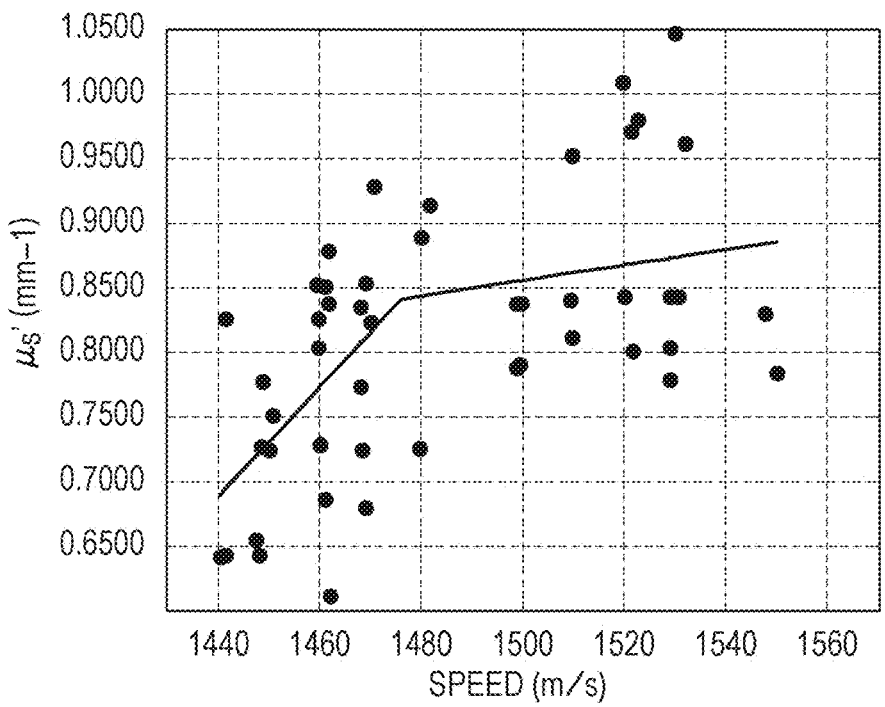

Alternatively, a relational expression in which two linear function approximate expressions are combined may be acquired and stored in the memory 710. For example, if the object is a breast, typically, the sound speed of the fat layer is in the range from about 1422 to about 1470 m/s, and the sound speed of the mammary gland layer is in the range from about 1510 to about 1530 m/s. Owing to this, the approximate expression may be switched in a range of the sound speed from 1470 to 1510 m/s. For example, when it is assumed that 1475 m/s is the border between the sound speed of the fat layer and the sound speed of the mammary gland layer, the expression may be divided into two approximate expressions. In this case, for the calculation results shown in FIGS. 4A and 4B, by obtaining a linear function approximate expression in a range of sound speed of 1475 m/s or lower and a linear function approximate expression in a range of sound speed higher than 1475 m/s, approximate expressions (graphs) shown in FIGS. 8A and 8B were acquired. Correlations R between the approximate expressions and calculation results shown in FIGS. 8A and 8B were R=0.7408 for the light absorption coefficient and R=0.5975 for the reduced scattering coefficient. In any case, a significant probability p is 0.000 or lower. As understood from the results, the correlation is higher for the relational expression acquired by the plurality of approximate expressions, as compared with the relational expression acquired by the single approximate expression. As described above, it is desirable to acquire the sound speed information from the optical coefficient information by using a relational expression with a high correlation value approximated by a plurality of approximate expressions. The border position of the sound speed may be changed in accordance with the structure of an object to be measured or data of the approximate expression stored in the memory 710. Also, without limiting to the combination of the two linear function approximate expressions, a relational expression in which a plurality of desirable approximate expressions are combined in accordance with an object may be used.

Alternatively, a plurality of relational expressions and a correlation value or a deviation value with respect to the plurality of relational expressions may be recorded in the memory 710, a relational expression that causes the correlation value to increase or the deviation value to decrease at an optical coefficient near the optical coefficient acquired by the optical coefficient acquiring unit may be selected, and the relational expression may be used for acquiring the sound speed information.

In addition to the optical coefficient and the sound speed, a relational table or a relational expression for parameters other than the sound speed, such as the wavelength, and tissue density, may be stored in the memory 710. If light with a plurality of wavelengths as described later in a third embodiment is used, since the optical coefficient depends on wavelength, a relational table or a relational expression between the sound speed and the optical coefficient for each wavelength of irradiation light may be prepared.

Also, if a breast is considered as the object, the relational table or the relational expression between the optical coefficient and the sound speed may be changed depending on the density of the mammary gland tissue (mammary gland density). That is, a relational table or a relational expression corresponding to the mammary gland density or the category of the mammary gland density may be saved in the memory 710. Then, the sound speed acquiring unit 740 may acquire information relating to the mammary gland density of the object, read out the relational table or the relational expression corresponding to the category of the mammary gland density of the object to be measured, and acquire the sound speed information by using the relational table or the relational expression. The information relating to the mammary gland density is a concept including the mammary gland density or the category of the mammary gland density.

According to Breast Imaging Reporting and Data System (BI-RADS), the mammary gland density is divided into four categories including a. uniform fatty mammary glands, b. scattered fatty mammary glands, c. mammary glands with high mammary gland density, and d. mammary glands with very high mammary gland density. The mammary gland density tends to increase in the order of the categories a, b, c, and d.

Figure 9:
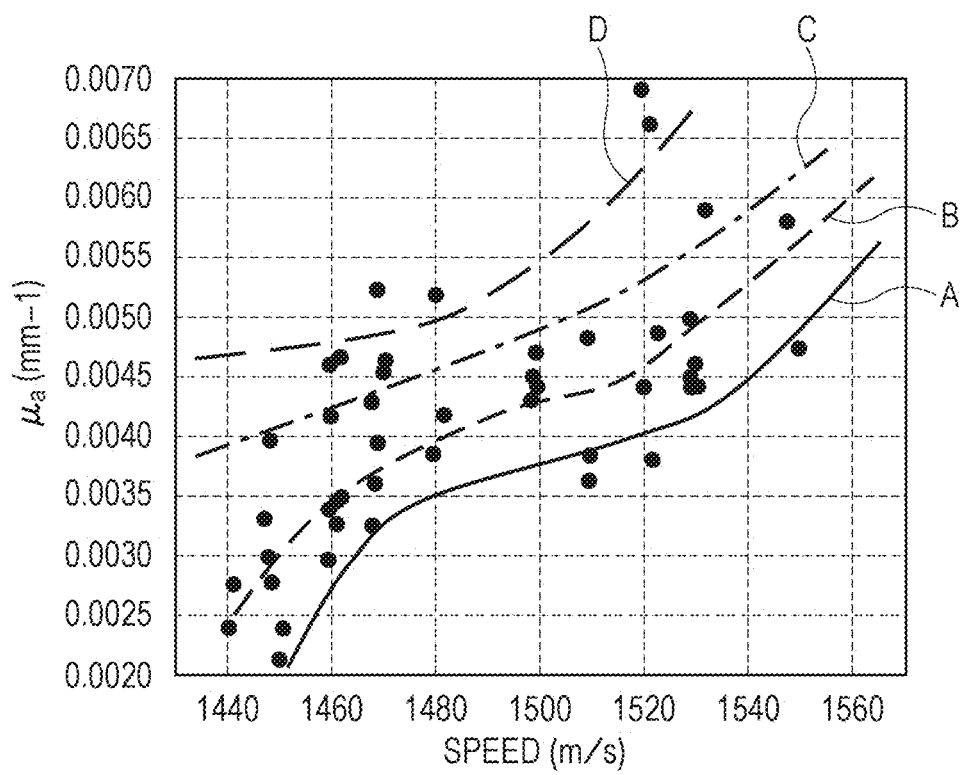
FIG. 9 is an illustration showing the relationship between the sound speed and the optical coefficient for each category of mammary gland density.

FIG. 9 is a graph representing the relationship between the optical coefficient and the sound speed for each category of mammary gland density with respect to the scatter diagrams shown in FIGS. 4A and 4B. The graphs corresponding to the above-described categories a to d of the mammary gland densities may be conceived as shown in the graphs shown in FIG. 9. Graph A corresponds to the category of a. uniform fatty mammary glands. Graph B corresponds to the category of b. scattered fatty mammary glands. Graph C corresponds to the category of c. mammary glands with high mammary gland density. Graph D corresponds to the category of d. mammary glands with very high mammary gland density.

As shown in FIG. 9, it is conceivable that the sound speed of an object with a low mammary gland density is low and the sound speed of an object with high mammary gland density is high when substantially equivalent optical coefficients are acquired. Owing to this, the relationship between the sound speed and the optical coefficient is different depending on the category. Owing to this, the sound speed acquiring unit 740 can acquire the sound speed information of the object with high accuracy by using the relational expression or the relational table corresponding to the mammary gland density while the mammary gland density serves as a parameter. The input unit 900 may be configured to allow the user to designate the mammary gland density or the category of the mammary gland density. Alternatively, the mammary gland density or the category of the mammary gland density may be estimated on the basis of image data acquired by a modality, such as X-ray mammography, MRI, or CT as a mammary gland density measuring unit. A relational table or a relational expression among the mammary gland density, wavelength, optical coefficient, and sound speed may be stored in the memory 710. Also, a relational table or a relational expression among a parameter that affects the sound speed, such as the age, sex, race, etc., and the optical coefficient, and the sound speed may be stored in the memory. The memory may store a relational table corresponding to a plurality of values of various parameters. The sound speed acquiring unit 740 may use at least one of the mammary gland density, wavelength, age, sex, and race as an input parameter in addition to the optical coefficient, read out a relational table or a relational expression corresponding to the input parameter, and acquire sound speed information.

The parameter to be additionally associated with the relational table or the relational expression between the sound speed and the optical coefficient may be designated by the user using the input unit 900. The sound speed acquiring unit may acquire the sound speed information by using the relational table or the relational expression corresponding to the parameter designated by the user.

Also, the relational table or the relational expression stored in the memory 710 may be re-written.

S400: Step of Acquiring Initial Sound Pressure Distribution

The initial sound pressure acquiring unit 730 serving as an object information acquiring unit acquires the initial sound pressure distribution in the object 1000 on the basis of the electric signal group stored in the memory 710, the sound speed information acquired in S300, and the position information of the respective receiving elements 411 to 414. For a method of reconfiguring the initial sound pressure distribution, a known reconfiguration method, such as a time domain reconfiguration method, a Fourier domain reconfiguration method, or a model base reconfiguration method (repetitive reconfiguration method) may be employed. For example, a time domain reconfiguration method called universal back-projection (UBP) as described in Physical Review E71, 016706 (2005) may be employed.

The initial sound pressure acquiring unit 730 may read out the position information of the respective receiving elements 411 to 414 previously stored in the memory 710. Alternatively, the initial sound pressure acquiring unit 730 may acquire the position information of the respective receiving elements 411 to 414 by receiving the position information of the receiving unit 400 from a position sensor included in the drive unit 500 upon light irradiation as a trigger.

S500: Step of Acquiring Light Fluence Distribution

A photoacoustic wave is generated when energy of absorbing light irradiated on an object is converted into a sound pressure. An initial sound pressure $P_0$ when a photoacoustic wave is generated can be expressed by Expression (1) as follows:

$$P_0(r) = \Gamma(r) \cdot \mu_a(r) \cdot \phi(r) \quad (1),$$

where r represents a position in the object, $P_0$ represents an initial sound pressure, which is acquired on the basis of a reception signal of a photoacoustic wave, $\Gamma$ is a Gruneisen coefficient, which is a known parameter uniquely determined when a tissue is determined, $\mu_a$ represents a light absorption coefficient, and $\phi$ represents a light fluence.

Referring to Expression (1), it is understood that the light fluence of the light emitted on the object at each position of the object has to be calculated, to acquire a light absorption coefficient distribution in the object.

The light fluence acquiring unit 750 serving as an object information acquiring unit acquires a light fluence distribution in the object 1000 of the light irradiated on the object 1000, on the basis of the optical coefficient information acquired in S200. That is, the light fluence acquiring unit 750 acquires the value of light fluence irradiated at each position in the object.

The light fluence acquiring unit 750 can acquire the light fluence distribution by a known method on the basis of the optical coefficient information. For example, the light fluence acquiring unit 750 may acquire the light fluence distribution on the basis of parameters, such as an in-plane intensity distribution of the light emitted from the light irradiation unit 100 and the shape of the object, in addition to the optical coefficient information. An intensity distribution acquiring unit (not shown) may acquire the in-plane intensity distribution of the light, and a shape acquiring unit (not shown) may acquire the shape of the object every measurement. Also, a light quantity meter (power meter) which is not illustrated may measure the total light quantity of the irradiation light. For the calculation method of the light fluence, the finite element method, the Monte Carlo method, etc., may be used. For example, the light fluence distribution may be acquired by a method described in Japanese Patent Laid-Open No. 2011-206192.

S600: Step of Acquiring Light Absorption Coefficient Distribution

The light absorption coefficient acquiring unit 760 serving as an object information acquiring unit acquires a light absorption coefficient distribution on the basis of the initial sound pressure distribution acquired in S400 and the light fluence distribution acquired in S500. The light absorption coefficient acquiring unit 760 divides the initial sound pressure $P_0$ at each position of the region of interest by the light fluence $\phi$ in accordance with Expression (1), and hence can acquire the light absorption coefficient $\mu_a$. On the basis of an assumption that the Gruneisen coefficient $\Gamma$ is known, the light absorption coefficient acquiring unit 760 may read out and use the Gruneisen coefficient previously stored in the memory 710 for the calculation.

In this embodiment, the light absorption coefficient distribution acquired in S600 is distribution information representing a value of a light absorption coefficient at each position of the object, and differs from the light absorption coefficient acquired on the basis of the assumption that the object is a uniform medium in S200. The receiving elements 411 to 414 for the photoacoustic wave have reception band characteristics. A reception band characteristic is a reception sensitivity characteristic for the frequency of a photoacoustic wave. The frequency band of a photoacoustic wave is different depending on the size of an optical absorber being a generation source of the photoacoustic wave. As the result, an optical absorber with a size which generates a frequency that can be received by a receiving element is mainly imaged. For example, when the center frequency of the reception band of a receiving element is 3 MHz and the sound speed of an object is 1480 m/s, the size of an optical absorber that can be measured by this receiving element is in a range from about 0.370 mm to about 1.48 mm. The size particularly suitable for the measurement is about 0.493 mm. That is, in this case, it is difficult to image an optical absorber having a size smaller than 0.370 mm and an optical absorber having a size larger than 1.48 mm. Hence, the light absorption coefficient distribution acquired by the photoacoustic measurement is a light absorption coefficient distribution having resolution depending on the reception band characteristic.

S700: Step of Displaying Image of Light Absorption Coefficient Distribution

The control unit 770 transmits data of the light absorption coefficient distribution of the object 1000 to the display unit 800, and causes the display unit 800 to display an image of the light absorption coefficient distribution, a numerical value of a specific position in the light absorption coefficient distribution, and so forth. If the object information is three-dimensional information, the control unit 770 can cause a tomography image cut along a desirable cross section, a maximum intensity projection (MIP) image, or an image processed by volume rendering to be displayed. For example, a 3-D image may be displayed in a plurality of different directions. Also, the user may change the gradient, display region, window level, and window width of the displayed image by using the input unit 900 while checking the display on the display unit 800. The control unit 770 may cause the display unit 800 to display the signal data acquired in S100, the optical coefficient information acquired in S200, the sound speed information acquired in S300, the initial sound pressure distribution acquired in S400, or the light fluence distribution acquired in S500. The input unit 900 may be configured to switch ON/OFF of the display of each piece of information. Also, for the display form, for example, superimposition display or parallel display may be employed.

With the photoacoustic apparatus according to this embodiment, the sound speed information close to the true value of the object can be acquired on the basis of the optical coefficient information of the object. Also, with the photoacoustic apparatus according to this embodiment, the initial sound pressure distribution as the object information can be acquired by using the sound speed information close to the true value acquired on the basis of the optical coefficient information. That is, with the photoacoustic apparatus according to this embodiment, object information with higher resolution and contrast than those of object information acquired by using a sound speed far from the true value of related art can be acquired.

Second Embodiment

In the first embodiment, the representative value of the sound speed based on the assumption that the object 1000 is a uniform medium is acquired as the sound speed information of the object. However, in this embodiment, an example is described in which distribution information representing a value of a sound speed at each position of the object 1000 is acquired as the sound speed information of the object. The apparatus configuration according to this embodiment is similar to that of the first embodiment. A portion different from the first embodiment is described below.

The optical coefficient acquiring unit 720 acquires an optical coefficient distribution of the object 1000 by a known method as described in S200.

The optical coefficient acquiring unit 720 may acquire the optical coefficient distribution on the basis of the signal data acquired by using the photoacoustic apparatus.

Alternatively, the optical coefficient acquiring unit 720 may acquire the optical coefficient information by inputting the optical coefficient distribution of the object measured by a diffuse optical tomography (DOT) apparatus.

Still alternatively, the optical coefficient acquiring unit 720 may acquire the optical coefficient information of the object 1000 on the basis of structure information of the object 1000 acquired by a modality other than the photoacoustic apparatus. A typical optical coefficient in each structure configuring a living body is known. Hence, for example, the structure of each position in the object acquired by analyzing an image acquired by another modality apparatus, such as an ultrasound diagnostic apparatus, MRI, or CT may be specified, the optical coefficient corresponding to each structure may be allocated, and thus the optical coefficient distribution may be acquired.

The light fluence acquiring unit 750 may acquire the light fluence distribution on the basis of the optical coefficient distribution of the object acquired by the optical coefficient acquiring unit 720. With this embodiment, since the optical coefficient information with regard to the non-uniformity of the optical coefficient in the object is used, the light fluence distribution can be acquired with hither accuracy than that of the first embodiment.

The sound speed acquiring unit 740 can acquire a value of a sound speed at each position of the object 1000 from the value of the optical coefficient at each position of the object 1000, in accordance with the relational expression or the relational table between the sound speed and the optical coefficient stored in the memory 710. That is, in this embodiment, the sound speed acquiring unit 740 can acquire a sound speed distribution of the object 1000 on the basis of the optical coefficient distribution of the object 1000. For example, the sound speed acquiring unit 740 replaces the value of the optical coefficient with the value of the sound speed at each position of the object in accordance with the relational expression or the relational table for each position of the object, and hence acquires the sound speed distribution of the object 1000 on the basis of the optical coefficient distribution of the object 1000.

The sound speed acquiring unit 740 may perform interpolation processing on the optical coefficient information acquired by the optical coefficient acquiring unit 720, and acquire the optical coefficient information having resolution equal to or higher than the resolution of the original optical coefficient information. Further, the sound speed acquiring unit 740 acquires the sound speed information on the basis of the optical coefficient information treated with the interpolation processing, and hence can acquire sound speed information having resolution higher than the resolution of the optical coefficient information acquired by the optical coefficient acquiring unit 720.

Alternatively, the sound speed acquiring unit 740 performs the interpolation processing on the acquired sound speed information, and hence can acquire sound speed information with resolution higher than the original resolution determined by the resolution of the optical coefficient information.

With any of these methods, even if the optical coefficient acquiring unit 720 acquires the optical coefficient information with low resolution, the sound speed acquiring unit 740 can acquire the sound speed information with high resolution. Accordingly, the sound speed information with high resolution can be acquired with a small amount of calculation. For the method of the interpolation processing, any interpolation processing, such as linear interpolation, cubic interpolation, spline interpolation, or nearest point interpolation may be used.

The initial sound pressure acquiring unit 730 can acquire an initial sound pressure distribution on the basis of the sound speed distribution of the object acquired as described above. In this embodiment, since the sound speed information with regard to the sound-speed non-uniformity of the object 1000 is acquired, the initial sound pressure acquiring unit 730 can acquire an initial sound pressure distribution with higher accuracy than that of the first embodiment, by using the sound speed distribution of the object 1000.

The light absorption coefficient acquiring unit 760 acquires the light absorption coefficient distribution on the basis of the initial sound pressure distribution acquired by the initial sound pressure acquiring unit 730, and the light fluence distribution acquired by the light fluence acquiring unit 750.

The control unit 770 causes the display unit 800 to display an image of the light absorption coefficient distribution, a numerical value of a specific position, and so forth. In this embodiment, the control unit 770 may cause the display unit 800 to display an image of the sound speed distribution acquired by the sound speed acquiring unit 740, a numerical value of a specific position, and so forth. Also, if only the sound speed distribution acquired by the sound speed acquiring unit 740 is displayed, the steps in S200 and S300 are executed, and the steps in S100, S400, S500, and S600 may be omitted.

Meanwhile, with this embodiment, the resolution of the sound speed information depends on the optical coefficient information. Owing to this, with this embodiment, by acquiring the sound pressure information on the basis of the optical coefficient information acquired by the method that can acquire the optical coefficient information with high resolution, the sound speed information with high resolution can be acquired.

In the sound speed distribution, a region with a known sound speed because the kind of the portion is previously known or due to other reason may be replaced with a known value regardless of the optical coefficient value.

The photoacoustic apparatus according to this embodiment can acquire the optical coefficient distribution of the object and acquire the sound speed distribution of the object from the optical coefficient distribution of the object. Accordingly, the light absorption coefficient distribution can be acquired with higher accuracy than that of the first embodiment, on the basis of the initial sound pressure distribution acquired with higher accuracy than that of the first embodiment and the light fluence distribution acquired with further high accuracy.

Third Embodiment

In this embodiment, an example is described in which spectral information, for example, information relating to the concentration of a substance configuring an object is acquired on the basis of a photoacoustic wave generated by irradiating the object with light with a plurality of mutually different wavelengths.

An operation of a photoacoustic apparatus according to this embodiment is described below with reference to a flowchart in FIG. 10. In this embodiment, a photoacoustic apparatus similar to that according to the first embodiment or the second embodiment is used.

In this embodiment, first, steps from S100 to S600 are executed by using light with a first wavelength $\lambda_1$, and a light absorption coefficient distribution corresponding to the first wavelength is acquired. The control unit 770 determines whether or not the measurement has completed for all wavelengths (S800). If the measurement for all wavelengths is not completed, the control unit 770 changes the wavelength of the light emitted from the light irradiation unit 100, and executes the steps from S100 to S600 again. That is, the steps from S100 to S600 are executed by using light with a second wavelength $\lambda_2$, and a light absorption coefficient distribution corresponding to the second wavelength is acquired. In this embodiment, the memory 710 stores a relational table or a relational expression between sound speed information and optical coefficient information corresponding to each of the plurality of wavelengths. Then, in S300, the sound speed acquiring unit 740 reads out the relational table or the relational expression corresponding to each wavelength from the memory 710, and acquires the sound speed information for each wavelength.

Then, the concentration acquiring unit 780 serving as an object information acquiring unit acquires an oxygen saturation distribution as information relating to the concentration of a substance configuring the object (S900). Hereinafter, an example of a method of acquiring an oxygen saturation distribution is described.

When $\lambda_1$ and $\lambda_2$ are wavelengths of irradiation light, and $\varepsilon_{Hb}$ is a molar light absorption coefficient [1/(mm·M)] of oxyhemoglobin and deoxyhemoglobin, $$\varepsilon_{HbO_2}$$

and when $C_{Hb}$ is a concentration [M] of each hemoglobin, $$C_{HbO_2}$$

a light absorption coefficient distribution $\mu_a$ corresponding to each wavelength is expressed by Expression (2).

$$\mu_a(\lambda_1,r)=\varepsilon_{Hb}(\lambda_1,r)\cdot C_{Hb}+\varepsilon_{HbO_2}(\lambda_1,r)\cdot C_{HbO_2}$$

$$\mu_a(\lambda_2,r)=\varepsilon_{Hb}(\lambda_2,r)\cdot C_{Hb}+\varepsilon_{HbO_2}(\lambda_2,r)\cdot C_{HbO_2} \quad (2)$$

An oxygen saturation SO2 is a ratio of the concentration of oxyhemoglobin with respect to the concentration of total hemoglobin, and hence is defined by Expression (3).

$$SO2 = \frac{C_{HbO_2}(r)}{C_{HbO_2}(r)+C_{Hb}(r)} \quad (3)$$

From Expression (2) and Expression (3), the oxygen saturation SO2 is expressed by Expression (4).

$$SO2 = \frac{-\varepsilon_{Hb}(\lambda_2)\mu_a(\lambda_1,r)/\mu_a(\lambda_2,r)+\varepsilon_{Hb}(\lambda_1)}{\varepsilon_{HbO_2}(\lambda_2)-\varepsilon_{Hb}(\lambda_2))\cdot \mu_a(\lambda_1,r)/\mu_a(\lambda_2,r)+\varepsilon_{HbO_2}(\lambda_1)-\varepsilon_{Hb}(\lambda_1)} \quad (4)$$

Since the molar light absorption coefficient is known, as it is understood from Expression (4), the concentration acquiring unit 780 can calculate the oxygen saturation distribution on the basis of the light absorption coefficient distribution corresponding to the first wavelength and the light absorption coefficient distribution corresponding to the second wavelength.

Also, if it is assumed that light propagation is planar, the light absorption coefficient ratio in Expression (4) can be obtained by Expression (5) as follows:

$$\mu_a(\lambda_1,r)/\mu_a(\lambda_2,r)=P_0(\lambda_1)\phi_0(\lambda_1)/P_0(\lambda_2)\phi_0(\lambda_2)\cdot \exp(\mu_{\mathit{eff}}(\lambda_1)d(r)-\mu_{\mathit{eff}}(\lambda_2)d(r)) \quad (5),$$

where d is a distance from a light irradiation position (object surface), and $\phi_0$ is a light fluence at the light irradiation position. In this case, as it is understood from Expression (4) and Expression (5), the oxygen saturation can be acquired from the difference between an equivalent attenuation coefficient with the first wavelength and an equivalent attenuation coefficient with the second wavelength. That is, a relational table or a relational expression between the sound speed information and the optical coefficient information may be stored in the memory 710 while the difference in the equivalent attenuation coefficient between the two wavelengths serves as the optical coefficient information.

In addition to the oxygen saturation, the concentration acquiring unit 780 can acquire data which can be acquired through comparison between data based on different wavelengths, such as the concentration of fat, collagen, water, hemoglobin, glucose, or molecular probe.

The control unit 770 causes the display unit 800 to display an image of the oxygen saturation distribution acquired by the concentration acquiring unit 780, a numerical value of a specific position, and so forth (S1000). An image of the initial sound pressure distribution or the light absorption coefficient distribution may be displayed together with the image of the oxygen saturation distribution.

Since the sound speed information has low wavelength dependency, the optical coefficient information corresponding to a partial wavelength of the plurality of wavelengths may be used for acquiring the sound speed information. Also, the sound speed information corresponding to a partial wavelength of the plurality of wavelengths may be used for processing on the reception signal of the photoacoustic wave corresponding to the residual wavelength. Also, the average value or median value of the sound speed information acquired from the optical coefficient information acquired with a plurality of wavelengths may be used for processing on the reception signal of the photoacoustic wave corresponding to the plurality of wavelengths.

For example, in this embodiment, the optical coefficient acquiring unit 720 acquires optical coefficient information corresponding to the first wavelength. Then, the initial sound pressure acquiring unit 730 may acquire an initial sound pressure distribution corresponding to the second wavelength on the basis of the sound speed information corresponding to the first wavelength and an electric signal corresponding to the second wavelength. Also, the sound speed acquiring unit 740 may acquire sound speed information corresponding to the second wavelength in accordance with a relational table or a relational expression corresponding to the second wavelength by using the optical coefficient information acquired on the basis of the electric signal corresponding to the first wavelength.

It is desirable to decrease the interval between measurement of the photoacoustic wave with the first wavelength and measurement of the photoacoustic wave with the second wavelength. If the measurement interval is increased, the object may more likely move. If the object moves, a shift may be generated in images between the wavelengths, and acquisition accuracy for information relating to the concentration may decrease. Owing to this, after the step in S100 is executed using the light with the first wavelength, the step in S100 may be executed using the light with the second wavelength before the other steps are executed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-249069 filed Dec. 21, 2015, which is hereby incorporated by reference herein in its entirety.

What is claimed is:

1. A photoacoustic apparatus comprising:
a memory storing a program; and
one or more processors which, by executing the program, function as:
a light irradiation unit configured to irradiate an object with light;
a receiving unit configured to convert a photoacoustic wave generated from the object irradiated with the light from the light irradiation unit into an electric signal;
an optical coefficient acquiring unit configured to acquire optical coefficient information of the object by analyzing distribution information generated from the electric signal;
a sound speed acquiring unit configured to acquire sound speed information of the object using the optical coefficient information acquired by the optical coefficient acquiring unit, by looking up a table defining a relationship between sound speed information and the optical coefficient information; and
an object information acquiring unit configured to acquire object information by using the electric signal and the sound speed information.

2. The photoacoustic apparatus according to claim 1, wherein the optical coefficient acquiring unit acquires a representative value of an optical coefficient of the object as the optical coefficient information.

3. The photoacoustic apparatus according to claim 2, wherein the sound speed acquiring unit acquires a representative value of a sound speed of the object as the sound speed information by using the representative value of the optical coefficient of the object.

4. The photoacoustic apparatus according to claim 1, wherein the object information acquiring unit acquires the object information by using the electric signal, the sound speed information, and the optical coefficient information.

5. The photoacoustic apparatus according to claim 1, wherein the object information acquiring unit
acquires an initial sound pressure distribution in the object by using the electric signal and the sound speed information,
acquires a light fluence distribution in the object by using the optical coefficient information, and
acquires the object information relating to a light absorption coefficient distribution in the object by using the initial sound pressure distribution and the light fluence distribution.

6. The photoacoustic apparatus according to claim 1, wherein the memory stores the table.

7. The photoacoustic apparatus according to claim 6, wherein the memory stores a plurality of the tables corresponding to information relating to different mammary gland densities, and
wherein the sound speed acquiring unit acquires the sound speed information by using the table corresponding to information relating to a mammary gland density of the object.

8. The photoacoustic apparatus according to claim 1, wherein the light irradiation unit irradiates the object with light with a plurality of mutually different wavelengths,
wherein the receiving unit converts photoacoustic waves generated from the object irradiated with the light with the plurality of wavelengths from the light irradiation unit into electric signals respectively corresponding to the plurality of wavelengths,
wherein the optical coefficient acquiring unit acquires optical coefficient information corresponding to a partial wavelength of the plurality of wavelengths,
wherein the sound speed acquiring unit acquires the sound speed information by using the optical coefficient information corresponding to the partial wavelength, and
wherein the object information acquiring unit acquires object information respectively corresponding to the plurality of wavelengths by using the sound speed information acquired by using the optical coefficient information corresponding to the partial wavelength and the electric signals respectively corresponding to the plurality of wavelengths.

9. The photoacoustic apparatus according to claim 8, wherein the object information acquiring unit acquires initial sound pressure distributions respectively corresponding to the plurality of wavelengths by using the sound speed information acquired by using the optical coefficient information corresponding to the partial wavelength and the electric signals respectively corresponding to the plurality of wavelengths,
wherein the optical coefficient acquiring unit acquires optical coefficient information respectively corresponding to the plurality of wavelengths,
wherein the object information acquiring unit acquires light fluence distributions respectively corresponding to the plurality of wavelengths by using the optical coefficient information respectively corresponding to the plurality of wavelengths, and
wherein the object information acquiring unit acquires object information by using the initial sound pressure distributions respectively corresponding to the plurality of wavelengths and the light fluence distributions respectively corresponding to the plurality of wavelengths.

10. An information acquiring apparatus comprising:
a memory storing a table defining a relationship between sound speed information and optical coefficient information;
an optical coefficient acquiring unit configured to acquire optical coefficient information of an object by analyzing distribution information generated from an electric signal, the electric signal having been converted from a photoacoustic wave generated from the object upon being irradiated with light; and
a sound speed acquiring unit configured to acquire sound speed information of the object using the optical coefficient information of the object acquired by the optical coefficient acquiring unit with looking up the table stored in the memory.

11. An information acquiring method comprising:
converting a photoacoustic wave generated from an object irradiated with light into an electric signal,
acquiring optical coefficient information of an object by analyzing distribution information generated from the electric signal; and
acquiring sound speed information of the object using the acquired optical coefficient information of the object by looking up a table defining a relationship between sound speed information and the optical coefficient information.

12. A non-temporary storage medium storing a program configured to cause a computer to execute the information acquiring method according to claim 11.

* * * * *